United States Patent [19]

Kostichka et al.

[11] Patent Number: 5,162,654

[45] Date of Patent: Nov. 10, 1992

[54] DETECTION APPARATUS FOR ELECTROHORETIC GELS

[75] Inventors: Anthony J. Kostichka; Lloyd M. Smith, both of Madison, Wis.

[73] Assignee: Wisconsin Alumni Research Foundation, Madison, Wis.

[21] Appl. No.: 650,393

[22] Filed: Feb. 1, 1991

[51] Int. Cl.$^5$ .......................................... G01N 21/64
[52] U.S. Cl. ............... 250/458.1; 250/461.2; 250/302; 204/182.8; 204/299 R
[58] Field of Search ............... 250/461.2, 461.1, 458.1, 250/302, 303; 204/299 R, 182.8

[56] References Cited

U.S. PATENT DOCUMENTS

| | | | |
|---|---|---|---|
| 4,649,280 | 3/1987 | Holland et al. | 250/487.1 |
| 4,675,095 | 6/1987 | Kambara et al. | 204/299 R |
| 4,707,235 | 11/1987 | Englert et al. | 204/182.8 |
| 4,811,218 | 3/1989 | Hunkapiller et al. | 204/299 R |
| 4,832,815 | 5/1989 | Kambara et al. | 204/299 R |
| 4,833,332 | 5/1989 | Robertson, Jr. et al. | 250/461.2 |
| 4,874,492 | 10/1989 | Mackay | 204/182.8 |
| 4,879,012 | 11/1989 | Kambara et al. | 204/157.15 |
| 4,881,812 | 11/1989 | Ohkubo et al. | 356/344 |
| 4,892,638 | 1/1990 | Watanabe et al. | 204/299 R |
| 4,904,366 | 2/1990 | Tokita et al. | 204/299 R |
| 4,909,920 | 3/1990 | Sarrine et al. | 204/299 R |
| 4,927,265 | 5/1990 | Brownlee | 356/72 |
| 4,960,999 | 10/1990 | McKean et al. | 250/461.1 |
| 5,006,716 | 4/1991 | Hall | 250/36.8 |

OTHER PUBLICATIONS

Connell et al., Automated DNA Sequence Analysis, *BioTechniques* 342, vol. 5, No. 4 (1987).

Drossman et al., High-Speed Separations of DNA Sequencing Reactions by Capillary Electrophoresis, *Analytical Chemistry (1990)*.

Luckey, et al., High Speed DNA Sequencing by Capillary Electrophoresis, *Nucleic Acids Research*, vol. 18, No. 15 (1990).

Smith et al., Fluorescence Detection in Automated DNA Sequence Analysis, *Nature*, vol. 321, No. 6071, pp. 674–679 (1986).

Smith, DNA Sequence Analysis: Past, Present, and Future, *American Biotechnology Laboratory*, vol. 7, No. 5 (May 1989).

*Primary Examiner*—Carolyn E. Fields
*Assistant Examiner*—Drew A. Dunn
*Attorney, Agent, or Firm*—Quarles & Brady

[57] ABSTRACT

An apparatus is disclosed to optically determine which of four fluorophores is attached to a band of DNA molecules on an electrophoresis gel. The apparatus includes four separate band pass interference filters and four wedge prisms to create four discrete areas of light on a detector. Digital comparison of the relative intensity of light sensed in the four discrete areas determines the identity of the excited fluorophore.

6 Claims, 2 Drawing Sheets

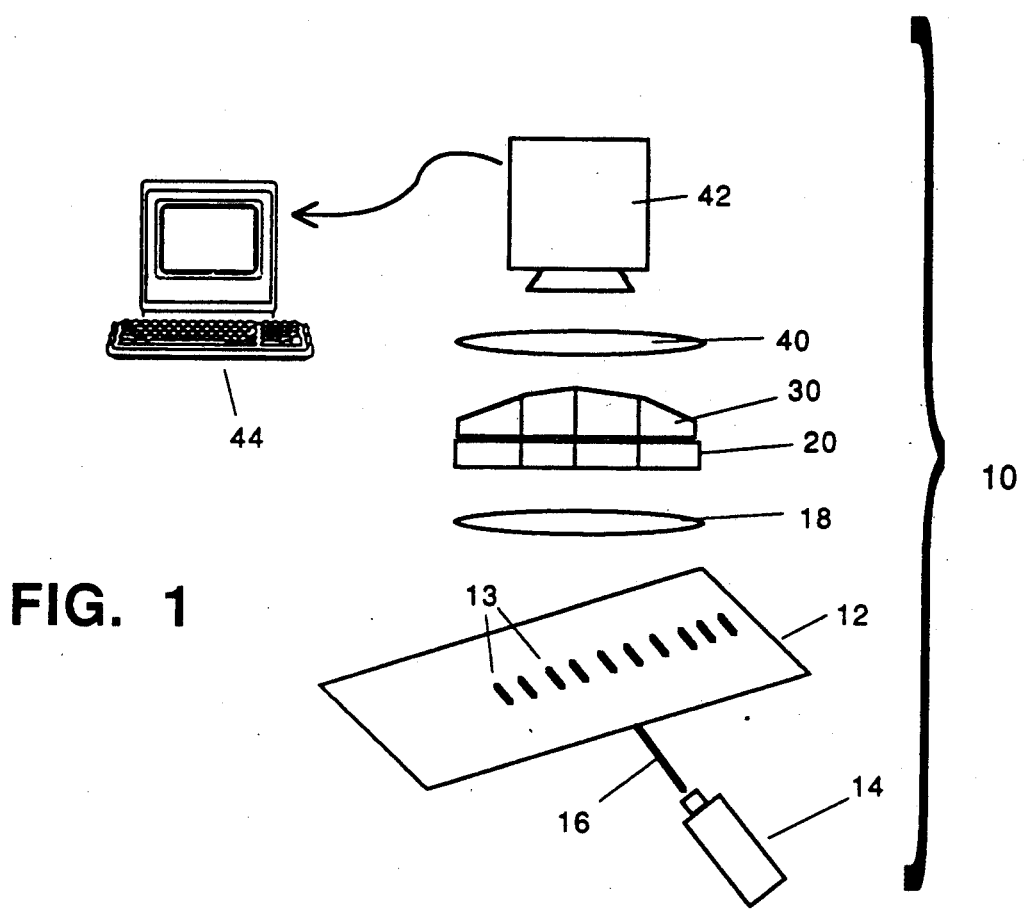
FIG. 1
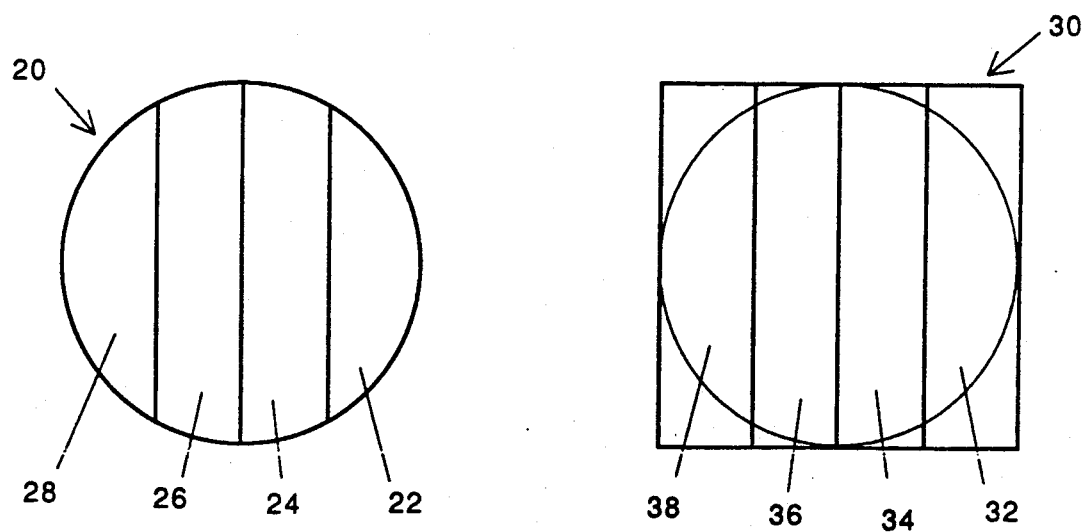
FIG. 2
FIG. 3

DETECTION APPARATUS FOR ELECTROHORETIC GELS

FIELD OF THE INVENTION

The present invention is directed to optical detecting systems for the analysis of multiple lanes of fluorescently labeled strands of nucleic acids separated on an electrophoretic gel.

BACKGROUND OF THE INVENTION

The revolution in modern biology in the past decades has been driven in large part by the development of an array of new methods and tools for the manipulation of molecules of DNA, the basic substance of molecular genetics. Included within the array of those tools has been the ability to determine the precise chemical structure of large DNA molecules. DNA molecules are linear chains in which the links in the chain are made up of a series of one of four chemical sub-units, referred to as nucleotides or bases, chemically fastened to a common backbone. Thus the structure of a large DNA molecule is determined by the sequence of the bases along the very long continuous DNA molecule. The ability to sequence DNA molecules is, in essence, the ability to read the genetic code and determine the structure of individual DNA molecules, which code for specific genes or traits.

Accordingly, much effort has been expended on methods for sequencing DNA. Two very different methods of sequencing DNA have been developed, and both methods may be performed manually in laboratories in which DNA is sequenced. As the needs for DNA sequencing have expanded from portions of genes to whole genes, and to greater and greater segments of DNA, the need for the automation of DNA sequencing operations has become apparent. As efforts are contemplated to determine the DNA sequence of the genome of whole organisms, beginning with bacteria and proceeding thereon to eukaryotic organisms and to humans, efficient apparatus for the reading of DNA sequences becomes essential to make such projects reasonably practical.

One of the more developed approaches to sequencing of DNA in a manner that is adaptable to automated reading makes use of the enzymatic method of DNA sequencing, in which DNA strands of varying lengths are initiated by a primer, each strand being terminated by a non-standard nucleotide which does not allow the extending DNA strand to proceed past that nucleotide. The result is a heterogeneous mixture of DNA strands of different lengths, each of which is terminated at a particular base. It is possible to make four different sets of such strands, with each set including only strands which terminate at a common base. The strands may be separated by length by performing an electrophoresis operation on the mixture of DNA strands. Such electrophoresis procedures separate the DNA by size, and have sufficient resolution that DNA segments which are only one base different in length can be readily separated in conventional electrophoresis gels. It also has become possible to appropriately label the primer DNA with fluorescent labels, or to label the bases with fluorescent labels, in such a fashion that each of the DNA strands associated with a particular base can be labeled with a different one of four fluorescent markers. By separating the segments of varying length in an electrophoresis gel, the gel can then be read automatically by optical systems which are sensitive to the fluorescence characteristics of the individual labels attached to the segments of DNA located on the gel. This general approach to the problem of DNA sequencing, and the fluorophores which may readily be used in it, are described in Smith, et al., Nature, 321:6071, pp. 674–679 (1986).

Apparatus have thus been developed in which DNA fragments can be detected in real time by scanning an electrophoresis gel, and identifying the DNA molecules as they pass the reading point in the gel. The particular identity of the DNA fragment which passes the gel is determined by the fluorescence characteristics of the particularly labeled DNA fragment. Apparatus of this general type have been commercialized. One is described in Connell et al., *BioTechniques*, 5:4 pp. 342–348 (1987). Another such apparatus is described in U.S. Pat. No. 4,832,815 to Kambara.

Desirable characteristics of an automated fluorescence detecting system for determining DNA sequences in such an electrophoresis gel include high sensitivity, a minimum of moving parts, and a good spectral separation of the detected signals, so that both maximum through-put and reliability of the overall instrument can be achieved. High sensitivity is important because the amount of DNA present in a band on a gel can be quite small, corresponding to less than $10^{-9}$ Molar concentration.

SUMMARY OF THE INVENTION

The present invention is summarized in that an instrument for the detection of the fluorescence pattern emitted by biological molecules on an electrophoresis gel which are tagged with one of four fluorophores includes an excitation laser to excite the fluorophores on the molecules; an interference filter assembly including four interference filters each selected to pass light in a wavelength band corresponding to the emission characteristics of the fluorophores; a prism wedge assembly which includes a respective prism wedge optically associated with each of the interference filters in the interference filter assembly to from the associated interference filter so that the light signals passing through the four interference filters are separated from each other; a light detector for detecting light incident thereon and for determining the relative intensity of the light incident thereon; and optical focusing means to direct fluorescence from the gel through the interference filter assembly and then through the prism wedge assembly to the detector so that the light incident to the detector is separated into four bands of different wavelengths, each of which is proportional to the intensity of the fluorescence from the gel.

It is an object of the present invention to provide a device for high speed multi-lane fluorescent detection of DNA electrophoresis gels for use in DNA sequencing operations.

It is another object of the present invention to provide a very sensitive high speed DNA detection operation, with a minimum of moving parts, and without requiring mechanical scan of the sample.

It is yet another object of the present invention to provide an optical detection system for the reading of DNA molecules on an electrophoresis gel which is extremely sensitive, so that less DNA is required for ready detection of the sequence, thereby permitting more efficient utilization of DNA in the procedure.

Other objects, advantages, and features of the present invention will become apparent from the following specification when taken in conjunction with the accompanying drawings.

BRIEF DESCRIPTION OF THE DRAWINGS

FIG. 1 is a schematic illustration of the elements of a preferred embodiment of a detection system according to the present invention.

FIG. 2 is a top plan view of the interference filter assembly of the system of FIG. 1.

FIG. 3 is a top plan view of the wedge prism assembly of the system of FIG. 1.

DESCRIPTION OF THE PREFERRED EMBODIMENT

Figure 4:
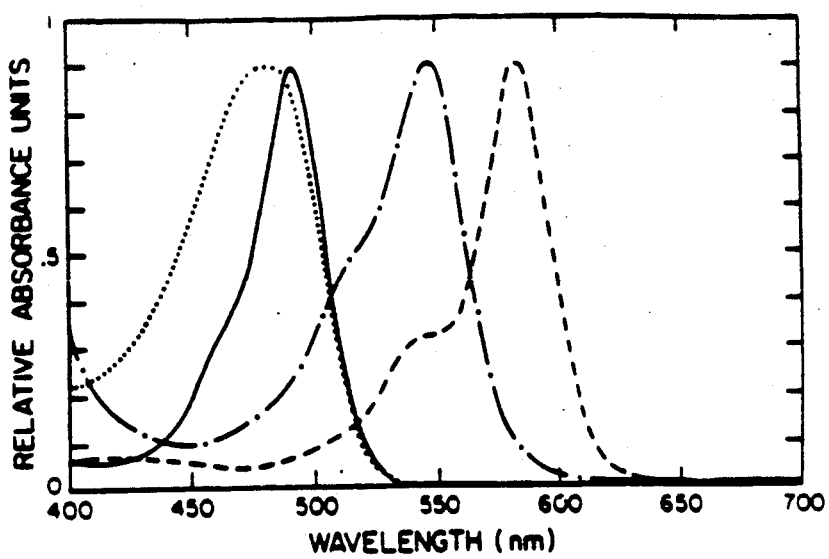
FIG. 4 is a graphical representation of the absorbence characteristics of four fluorophores which may be used in the system of FIG. 1.

Shown in FIG. 1 is a schematic illustration for the optics of the electrophoresis gel detection system of the present invention. This system is intended to facilitate the reading of DNA sequences, by the optical reading in real time of electrophoresis gels created during the process of sequencing DNA. The apparatus is particularly constructed so as to be able to quickly and accurately differentiate the fluorescence patterns emitted by bands of fluorescently-labeled DNA carried on such an electrophoresis gel.

Referring in detail to the schematic illustration of FIG. 1, the apparatus generally is indicated at 10. Indicated at 12 is an electrophoresis gel assembly. This assembly consists of a large rectangular gel, typically surrounded by a retaining structure, with an electrical field applied along the long axis of the rectangle. It is preferred within the practice of the present invention, and illustrated in the apparatus of FIG. 1, that the electrophoresis gel be a horizontally aligned apparatus. At one end of the gel, a mixture of DNA strands of different lengths is introduced. It is preferred here that the DNA be prepared in such a fashion that fluorescent markers are attached to the sets of DNA segments which are derived in reactions terminated by specific nucleotides. This process will be described in greater detail below.

Shown on the electrophoresis gel 12 are a series of bands 13 of DNA. These bands 13 represent the groups of DNA strands which are separated by size, each band representing a group of DNA strands having the same number of nucleotide bases. The set of bands move across the electrophoresis gel, under the force of the electric field, in a linear pattern referred to as a lane. While only one lane is illustrated in FIG. 1, it is to be understood that normally many such lanes will be resolved on a single electrophoresis gel.

Located to one side of the electrophoresis gel is an excitation or illumination device, such as a laser 14. The laser 14 directs a beam of light 16 horizontally into the edge of the electrophoresis gel. It is understood that it is not required that laser light be utilized, but simply that excitation means be used which generates excitation light of an appropriate wavelength to excite the fluorescent molecules attached to the DNA strands carried on the electrophoresis gel. Although a laser 14 is preferred as the excitation means, the laser light may be directed into the gel in any number of ways. The light is directed into the side of the gel in FIG. 1, but this method is illustrated only because of its simplicity. Other techniques include a laser light passed through a cylindrical lens to generate a fixed strip of light which could be directed downward onto the top glass plate of the electrophoresis gel, and a laser light directed against a scanning mirror which pivots to create a scanning beam traversing the area of excitation on the gel.

Located above the electrophoresis gel is a first focusing camera lens 18. The camera lens 18 is a multiple lens optical system of a kind which is readily available from commercial sources, such as Nikon. Located next above the camera lens 18 is an interference band-pass filter assembly 20. The filter assembly 20, which is also viewed in FIG. 2, is an optical component which is laterally split into four adjacent segments, as can be viewed in FIG. 2. Also indicated by the circular line in FIG. 2 is the profile of the optical window through which light reaches the filter assembly 20. In FIG. 2 the four segments of the assembly 20 are labeled 22, 24, 26, and 28. Each of the segments 22, 24, 26, and 28 is a different interference or band-pass filter constructed to pass through light only of a specific pre-selected frequency band. The selection of the wavelength band passed through each of the filter segments is intended to provide information sufficient to differentiate the four fluorescent markers. For the purposes of the embodiment of FIG. 1, as will be described in detail below, the band pass characteristics of the filter segment 22 are centered on light of a wavelength of 540 nanometers, the filter segment 24 is intended to pass light of 560 nanometers, the filter segment 26 is constructed to pass light centered on a wavelength of 580 nanometers, and the filter segment 28 is constructed so as to pass through light only centered on a wavelength of 610 nanometers.

Located above the filter assembly 20 is a prism wedge assembly 30. FIG. 3 illustrates a top plan view of the wedge assembly 30, and in FIG. 3, the circle illustrates the optical window of the light through the wedge assembly. It can readily be noted that the size and location of the parts of the wedge assembly in the optical window correspond to the size and location of the segments in the filter assembly of FIG. 2. The filter prism assembly 30 is also divided into four segments labeled 32, 34, 36, and 38, although in this instance the segments do not have optical characteristics of filters. Instead, as can be viewed best in FIG. 1, the individual elements of the prism wedge assembly 30 are constructed with canted upwardly facing surfaces so as to divert the light transmitted through the interference filter assembly 20 at predefined angles, all of which are canted outward from the vertical central axis of the apparatus of FIG. 10. The prism wedges 34 and 36 have a slight and opposite outward cant and the prism wedge 32 and 38 have a greater, and again opposite, outward cant. Above the prism wedge assembly 30 is a second camera focusing lens 40. Above the lens 40 is an optical camera 42, which preferably encompasses within it a CCD, or charge coupled device detector, which is capable of converting light into electronic images which can readily be scanned and stored in an electronic digital computer, indicated at 44, which is attached to the camera 42. The CCD detector 42 is a frame transfer CCD device to facilitate the timing of data transfer from it to the computer 44. The CCD detector, which has a field of 288 by 384 pixels, is cooled by thermoelectric cooling to −45° C. to minimize noise.

In the operation of the apparatus of FIG. 1, it is generally intended that it be utilized for automated fluorescence-based DNA sequence analysis. DNA sequencing may be performed by the so-called enzymatic method, which begins with a DNA sequence of unknown characteristics which is processed to be in a single stranded condition and which is then placed in four reaction vessels. In each reaction vessel, a DNA primer complementary to DNA adjacent to one end of the unknown DNA initiates an elongation of the opposite DNA strand to the unknown DNA in the presence of nucleotide triphosphate substrates, which are coupled enzymatically to the elongating second strand. By including in the enzymatic reaction mixture a small amount of a modified nucleotide, which lacks a 3' hydroxyl group, the opposite strands created by the primer elongation are all eventually terminated. If the modified nucleotide in each of the four reaction vessels is only a single one of the four possible nucleotides, all of the strands thus produced in a single reaction vessel will be terminated at a site at which that particular nucleotide is present. By performing four separate reactions of this type with a different one of the four nucleotides being modified in each reaction vessel, a group of four sets of elongated DNA strands can be created. In each set, each DNA strand is terminated by a nucleotide analog specific for one of the four bases. This results in a collection of fragments, each set of fragments terminating at only one of the four possible bases of a DNA sequence. For automated DNA sequencing, this procedure is modified by tagging the DNA strands with a fluorescent marker or fluorophore. This can be done by tagging either the primer for DNA elongation with the fluorophore or by coupling the fluorescent marker to the modified nucleotide lacking the 3' hydroxyl group. Using either approach, all the strands in the four sets of fragments are each coupled to a different one of the four fluorescent markers utilized.

The practice of the present invention requires the use of four fluorescent markers, or fluorophores. One set of possible fluorophores are those described by Smith. The four fluorescent markers described therein are fluorescein, NBD, tetramethyl-rhodamine and Texas Red. These fluorophores are useful since all are capable of absorbing input light in a common range of excitation wavelengths, and each fluoresces at a slightly different frequency peak. This may be best understood by referring to FIGS. 4 and 5. Shown in FIG. 4 is a spectral graph illustrating the relative absorption patterns for the four fluorescent markers. As can be viewed in FIG. 4, the four characteristic absorption spectra of the four dyes overlap. The absorption characteristic of fluorescein is indicated by the solid line, while the absorption spectrum of NBD is indicated by the curve which is totally dotted. The absorption spectrum of tetramethyl-rhodamine is indicated by the line which contains alternate dashes and dots, and the absorption characteristic of the Texas Red fluorescent marker is indicated by the curve which is entirely dashed. The same styles of lines for each fluorophore are used in FIG. 5 which illustrates the fluorescent emission spectra of the same four dyes. Note that all of these dyes absorb at a lower wavelength, and emit or fluoresce at a slightly higher wavelength. Thus, the optical excitation provided by the laser 14 can be selected to be generally below the peaks of the average fluorescence spectra of the four dyes. In the preferred embodiment of the present invention, the laser 14 can be selected to be a multiline argon ion laser which is emitting light at a wavelength of both 488 and 514 nanometers.

Other sets of fluorophores may also be used and may, in fact, be preferred. Applied Biosystems, Inc. of Foster City, California, U.S.A., sells a set of four fluorophores under the tradenames "Fam," "Joe," "Tamra" and "Rox." The fluorophores fluorescein, tetramethyl-rhodamine and Texas Red are available from Molecular Probes of Junction City, Oregon.

When DNA molecules are created for the DNA sequencing operation, they are separated on the electrophoresis gel 12. The object of the apparatus of FIG. 1 is to determine optically which one of the four fluorescent markers is attached to a band on the electrophoresis gel 12 as it passes by the region which is optically stimulated by the light from the laser 14. Thus the remaining optical components of the apparatus 10 are intended to detect and discriminate between the light emitted by the fluorescing dyes, in a rapid, sensitive, and efficient manner.

Thus, the four interference band pass filters which make up the filter assembly 20 are each selected so as to pass through light of a selected band associated with each of the fluorescent dyes attached to the DNA molecules. Since a portion of the laser excitation light is at 514 nanometers, the selection of band passes for the interference filters must be selected to avoid that wavelength. It is for that reason that the four band pass filters were selected to be 540, 560, 580, and 610 nanometers, each of which is thus somewhat higher than the excitation frequency, but which together permit the discrimination of the fluorescence patterns of the fluorophores.

Thus, the purpose of the interference filter assembly 20 is to sample the emission spectrum of the fluorescing gel only in four discrete spectral bands. In other words, rather than attempting to sample the entire spectrum of light emitting from the gel, this system samples that light only in four discrete separate bands. The fluorophores attached to the DNA molecules can still readily be distinguished based only on the information from these four sampled bands, as will be shown below.

The purpose of the prism wedge assembly 30 is to physically separate the light passing through each of the interference filters 20. The four separate light beams are physically separated so that they can be resolved and analyzed separately when finally detected by the CCD detector device 42. The purpose of the camera lenses 18 and 40 is to properly collect, collimate and focus the light through the system and into the CCD detector 42.

Note from FIG. 1 that the two central prism wedges 34 and 36 are canted downward at acute angles from the horizontal which are symmetrical and opposite. Thus the vertically directed light rays passing through the filters 24 and 26 will be bent away from vertical by equal and opposite angles. Similarly, the two outer prism wedges 32 and 38 are canted downward at greater acute angles which are again symmetrical and opposite. Thus the light passing through the filters 22 and 28 will also be deflected away from the vertical by equal and opposite angles.

Figure 6:
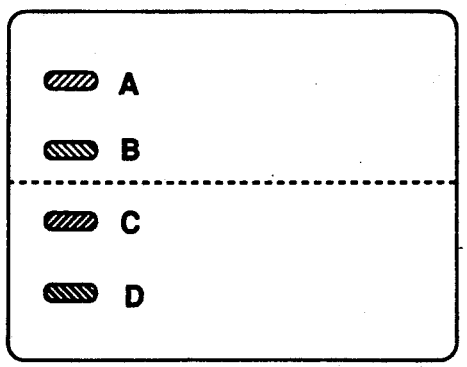
FIG. 6 is an illustration of the spatial separation of optical patterns achieved by the system of FIG. 1.

The result is illustrated schematically in FIG. 6. This figure is intended to illustrate the areas of light impinging on the detector 42. The light impacts the detector 42 in one or more of four possible locations designated A, B, C, and D. These four regions are the only locations on the CCD detector 42 in which light can be present.

Also shown in FIG. 6 is a dotted centerline, which indicates the vertical centerline where the light would have impacted the detector had it not been deflected. The output from each one of the interference filters has been separated by the prism wedge assembly 30, vertically as viewed in FIG. 6, into the areas A through D. Thus at each one of the locations A through D an amount of light will be present which is proportional to the excitation emitted from the gel in the specific band which is passed through the appropriate one of the interference filters 22, 24, 26, or 28.

This may be best understood by reference to a particular dye emission spectra. If, for example, a DNA band is passing through the scanning region of the electrophoresis assembly to which has been attached the fluorescent marker fluorescein, the DNA band would fluoresce with the fluorescent characteristics, indicated by the solid line in FIG. 5. Four spectral portions of the emitted light from the fluorophore would be passed through the band pass filters, and would be separated by the prism assembly, so as to be detected by the CCD detector 42. The CCD detector 42 would, for example, see at location D, the light signal passed by the 540 nanometer filter, at location A the light emission received through the 560 nanometer filter, at location B the light emission which passed through the 580 nanometer interference filter, and, finally, at location C, a light signal proportional to the amount of light passed through the 610 nanometer interference filter. If the light emitted from the gel matched the fluorescein fluorescent emission characteristics as illustrated in FIG. 5, the intensity of the light at each of those four locations would be in the relative proportion with the most light being detected at location D, the next most being at location A, the next most being at location B, and the least intense light signal being received at location C.

Figure 5:
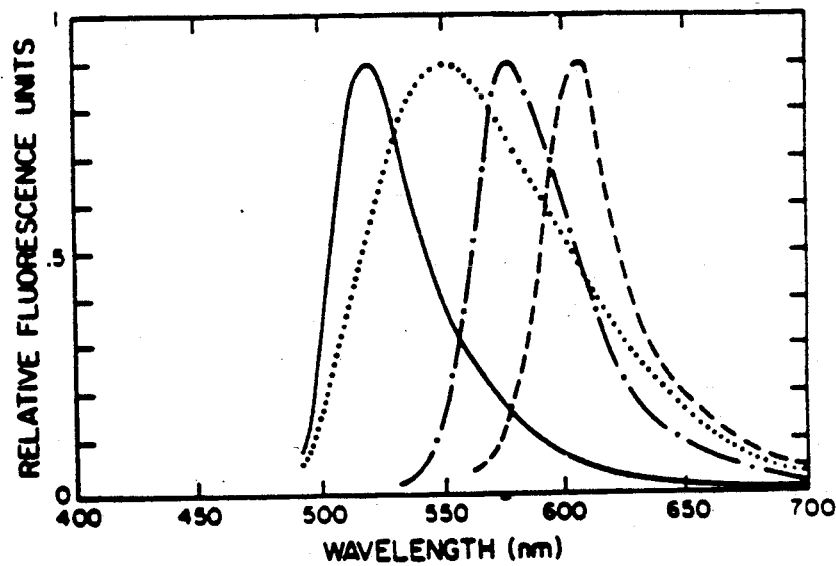
FIG. 5 is a graphical representation of the fluorescence characteristics of the same four fluorophores.

By contrast, if the DNA fluorescing was tagged with the fluorescent marker Texas Red, by reference to the emission spectra of Texas Red as illustrated in FIG. 5, it becomes clear that the emission spectra would be most intense at 610 nanometers, which is located at location C and least intense, if detectable at all, at location D. Similarly, for the fluorophore NBD, the signal detected would be most intense at A, moderately intense at B and D, and less intense at C. For the final fluorophore tetramethyl-rhodamine, the detected light would be most intense at B, less intense at A and C, and much less intense at D. Thus by digitizing the perceived intensity of the light signal at each of locations A, B, C and D, it is possible, under software control, to make a comparison of the measured intensity values to determine which of the four fluorophores is passing through the excitation region at that given instant.

Note that the absolute levels of fluorescence emission by the fluorophores is not important to this determination. The relative levels of sensed light at the four locations indicates the identity of the fluorophore, not the absolute intensity of the received light. This helps to make this system less prone to inaccuracies and errors due to variations in the amounts of fluorophores in the sample and aids in the accuracy of the system.

The image of the type shown in FIG. 6 is sensed on the detector array of the CCD detector 42. The array is scanned, as is normal, and the intensity of light received at each of the four locations is measured. The digital values representing this intensity are stored in the computer 44. The comparison of these stored digital values can then be done under software control, and the comparison will reveal the fluorophore, and therefore the DNA base, as it passes the detector in real time.

Note that the separation achieved by the prism wedges aids in the digital analysis of the received raw data. Since there is an area of no light signal between each of the locations A through D, the software can readily ascertain from the scanned digital data where the received light bands at each of the four locations are stored. It is also to be understood that although FIG. 6 shows the four light band locations for only a single DNA band on the electrophoresis gel, multiple lanes can be scanned and detected in parallel, it being required only that the scanning field of the detector 42 be large enough to scan the light output from several lanes in parallel. The adjustable focus provided by the camera lenses 18 and 40 serves to focus the light bands A through D onto the detector.

One of the principle advantages of the detection system of the present invention is that it is well adapted for high speed operation. Since the optics contains no moving parts, the speed of the reading of data is limited only by the speed of detection and scanning of the detector 42. Since there is no scanning or sampling of light from the gel, no bands will be missed. When used with a high speed thin horizontal electrophoresis gel separating 50 lanes of DNA, it may become possible to sequence as much as 20,000 bases of DNA in a single one hour long gel. This performance is more than an order of magnitude improvement over current commercial systems.

It is understood that the present invention is not limited to the particular arrangement of parts illustrated herein but embraces all modified forms thereof as come within the scope of the following claims.

We claim:

1. An instrument for the detection of the fluorescence pattern emitted by biological molecules on an electrophoresis gel which are tagged with one of four fluorophores comprising:

excitation means to excite the fluorophores on the molecules;

an interference filter assembly which includes four interference filters selected to pass light in a wavelength band corresponding to the emission characteristics of the fluorophores;

a prism wedge assembly which includes a respective prism wedge optically associated with each of the interference filters in the interference filter assembly to bend the light signal from the associated interference filter so that the light signals emitted by the four interference filters are separated from each other;

a light detector for detecting light incident thereon and for determining the relative intensity of the light incident thereon; and optical focusing means to direct fluorescence from the gel through the interference filter assembly and then through the prism wedge assembly to the detector so that the light impinging on the detector is separated into four bands, each of which is related to the intensity of the fluorescence from the gel in one of the wavelength bands associated with one of the interference filters.

2. An instrument as claimed in claim 1 wherein the excitation means is a laser.

3. An instrument as claimed in claim 1 wherein the interference assembly is made up of four laterally adjacent interference filters.

4. An instrument as claimed in claim 3 wherein the interference filters pass light at wavelengths centered at 540, 560, 580 and 610 nanometers respectively.

5. An instrument as claimed in claim 1 wherein the light detector is a CCD camera.

6. An instrument as claimed in claim 1 further comprising a digital computer to collect the data from the detector, the computer programmed to make a digital comparison of light received at discrete locations on the detector.

* * * * *

UNITED STATES PATENT AND TRADEMARK OFFICE
CERTIFICATE OF CORRECTION

PATENT NO. : 5,162,654 Page 1 of 1
DATED : November 10, 1992
INVENTOR(S) : Anthony J. Kostichka and Lloyd M. Smith It is certified that error appears in the above-identified patent and that said Letters Patent is hereby corrected as shown below:

Column 1,
Line 12, please insert therefor the following:
-- STATEMENT REGARDING FEDERALLY SPONSORED RESEARCH OR DEVELOPMENT
This invention was made with United States government support awarded by the following agencies: NIH IR01GM42366-01 and NSF DIR 8957582. The United States has certain rights in this invention. --

Signed and Sealed this

Ninth Day of August, 2005

JON W. DUDAS
*Director of the United States Patent and Trademark Office*